United States Patent [19]
Li et al.

[11] Patent Number: 6,136,814
[45] Date of Patent: Oct. 24, 2000

[54] AQUEOUS ACYCLOVIR PRODUCT

[75] Inventors: Jane Huey-Jiuan Li, Vernon Hills; Jouhn-Wern Jang, Lisle, both of Ill.

[73] Assignee: Fujisawa USA, Inc., Melrose Park, Ill.

[21] Appl. No.: 08/986,424

[22] Filed: Dec. 8, 1997

[51] Int. Cl.$^7$ .............................. A01N 43/90; B29D 22/00
[52] U.S. Cl. ...................... 514/262; 428/35.7; 428/36.8
[58] Field of Search ........................ 514/262; 428/35.7, 428/36.8

[56] References Cited

U.S. PATENT DOCUMENTS

| | | | |
|---|---|---|---|
| 4,671,331 | 6/1987 | Pruden | 141/98 |
| 4,724,232 | 2/1988 | Rideout et al. | 514/50 |
| 4,879,286 | 11/1989 | Alam et al. | 514/110 |
| 4,879,308 | 11/1989 | Alam et al. | 514/509 |
| 4,915,956 | 4/1990 | Alam et al. | 424/649 |
| 5,084,480 | 1/1992 | Pai et al. | 514/554 |

FOREIGN PATENT DOCUMENTS

| | | | |
|---|---|---|---|
| WO 96/35412 | 11/1996 | WIPO | A61K 9/127 |
| WO 97/00670 | 1/1997 | WIPO | A61K 9/06 |
| WO 97/17934 | 5/1997 | WIPO | A61J 1/00 |
| WO/97/17934 | 5/1997 | WIPO | A61J 1/00 |

OTHER PUBLICATIONS

Das Gupta et al 112CA:104740p, 1990.
Wesolowski et al 108CA:81934F, 1988.

*Primary Examiner*—Russell Travers
*Attorney, Agent, or Firm*—Leydig, Voit & Mayer, Ltd.

[57] ABSTRACT

The present invention provides a pharmaceutical product comprising an aqueous solution of acyclovir sodium contained within a sealed container constructed of an alkali resistant polymer having a $CO_2$ permeation constant of not more than about $1 \times 10^{-8}$ cc/cm$^2$/mm/sec/cmHg.

The present invention further provides a ready-to-use aqueous acyclovir product for parenteral administration with improved shelf life. The present invention further provides a method of storing aqueous acyclovir sodium, a method of maintaining the pH of aqueous acyclovir sodium, a method of preventing the precipitation of acyclovir from aqueous acyclovir sodium, and a method of preventing the influx of $CO_2$ in an aqueous acyclovir solution, which methods comprise storing aqueous acyclovir sodium according to the present invention.

36 Claims, 1 Drawing Sheet

AQUEOUS ACYCLOVIR PRODUCT

TECHNICAL FIELD OF THE INVENTION

The present invention relates to aqueous acyclovir sodium formulations and methods for storage thereof.

BACKGROUND OF THE INVENTION

Acyclovir, 2-amino-1,9-dihydro-9-[(2-hydroxy-ethoxy)methyl]-6H-purin-6-one, is an antiviral agent that has been known for approximately twenty years. There are three principal acyclovir formulations that are commercially distributed: a tablet for oral administration, a cream formulation for topical administration, and a lyophilized powder for parenteral administration. Production of the lyophilized powder is expensive, requiring cost-intensive processes such as, for example, vacuum-freezing and specialized equipment such as, for example, condensers and lyophilization chambers. Additionally, the equipment must be operated under sterile conditions, further increasing the cost of the product. For medical applications, the lyophilized powder must be properly reconstituted immediately prior to parenteral administration to a patient in need thereof.

There are many problems associated with the reconstitution of acyclovir. The reconstitution of acyclovir, which is time consuming and labor intensive, must be carried out by a medical professional, resulting in the inefficient consumption of the medical professional's time. Further, reconstitution sometimes gives formulations with particulate matter, requiring the interpretation of the medical professional. Such labor and time burden with respect to the medical professional's time increases the overall cost of the treatment to the patient.

Further, due to human error and varying degrees of skill among medical professionals, there is an increased risk of contamination during the reconstitution process. If the reconstitution is not performed aseptically, there is an increased risk of contamination of the formulation by harmful pathogens such as, for example, bacteria. Such contamination can result in harm to the patient, who may already be in a medically compromised state. Even if the reconstitution is performed aseptically, there remains a risk that the reconstitution will not be performed properly, for example, if the medical professional uses the wrong diluent or the wrong quantity of diluent. If the wrong diluent is used, the entire formulation could be medically ineffective, and possibly harmful, to the patient. If the correct diluent is used, but in incorrect ratio with respect to the acyclovir sodium, problems with concentration and/or solubilty can occur. As a result, there is a risk of variability in the safety and efficacy of the reconstituted product.

Another problem with reconstitution is the increased potential for safety hazards to the medical professional. Since reconstitution of acyclovir typically involves spikes and/or needles and puncturing of the container septa therewith, the medical professional is exposed to an increased risk of receiving a needle/spike stick. Such hazards are not only detrimental to the safety of the medical profession, but also are further complicated by the administrative costs related to the reporting, tracking, and documentation of facts surrounding needle/spike sticks, as required by most medical facilities. As a result, there is an increase in the overall cost of treatment, which ultimately falls on the patient.

Since aqueous solutions which contain an appreciable concentration of acyclovir require high pH, standard glass container incompatibility precludes long term storage of such solutions in a ready-to-use formulation. The pH required to maintain an aqueous solution of acyclovir is typically greater than about 10–11, depending on the desired concentration of acyclovir, due to the enormously greater aqueous solubility of the salt of acyclovir relative to the virtually insoluble undissociated form. The pH of aqueous acyclovir sodium, a highly alkaline compound, necessarily increases with increasing concentration of acyclovir. Since there is a great difference in solubility between acyclovir sodium and undissociated acyclovir, lowering the pH of the formulation would not be desirable due to precipitation of the relatively insoluble undissociated acyclovir. Such precipitation would make the formulation unacceptable for parenteral administration.

The incompatibility of glass at high pH conditions is well known. When a highly alkaline solution comes in contact with glass, alkaline attack upon the glass (generally by hydroxide ion) occurs within a relatively short time, resulting in the extraction of ions and the dislodging of glass flakes from the surface, thereby contaminating the solution. Even small amounts of such ions or particulate matter in an aqueous pharmaceutical solution can render it unacceptable for parenteral administration. The shelf life of reconstituted aqueous acyclovir in glass vials is evident from the instructions which accompany the package inserts. For example, according to the package insert, lyophilized acyclovir sold under the trademark Zovirax® sterile powder (Burroughs Wellcome), which is reconstituted in glass vials, must be used within twelve hours after reconstitution.

Some plastics may exhibit incompatibility problems as well. While some plastics contain polymers which are resistant to alkaline conditions, many standard plastics often contain monomers, plasticizing agents, processing agents (e.g., lubricants) and other materials which are released when the plastic comes into contact with an alkaline solution.

In view of the foregoing problems, there is a need for a ready-to-use acyclovir formulation for parenteral administration which does not require reconstitution prior to the administration thereof. Further, there exists a need for a cost effective method of storing aqueous acyclovir sodium solutions that will result in prolonged shelf life, yet will not produce container or drug-related particulate matter. There also exists a need for a cost effective alkali stable pharmaceutical product which enables the long term storage of aqueous acyclovir sodium at high pH. The present invention provides such a method and product. These and other advantages of the present invention, as well as additional inventive features, will be apparent from the description of the preferred embodiments provided herein.

BRIEF SUMMARY OF THE INVENTION

The present invention provides a pharmaceutical product comprising an aqueous solution of acyclovir sodium contained within a container constructed of an alkali resistant polymer having a $CO_2$ permeation constant of not more than about $5 \times 10^{-8}$ $cc/cm^2/mm/sec/cmHg$, wherein "cc" is the volume of $CO_2$ in cc; "$cm^2$" is the surface area of the polymer in $cm^2$; "mm" is the thickness of the polymer in mm; "sec" is the time in seconds; and "cmHg" is the pressure in cm Hg. The container is sealed with a seal which has a $CO_2$ permeation constant which does not substantially exceed the $CO_2$ permeation constant of the polymer.

The present invention further provides a pharmaceutical product with a shelf life of at least about 18 months comprising an aqueous solution of acyclovir sodium of predetermined volume and concentration, such that the pH of the solution due to $CO_2$ permeation does not fall below the pH of precipitation ($pH_p$) for at least about 18 months.

The present invention further provides a method of storing an aqueous solution of acyclovir sodium, wherein a predetermined volume of aqueous acyclovir sodium is placed in a container constructed of a polymer having a $CO_2$ permeation constant of not more than about $3 \times 10^{-8}$ cc/cm²/mm/sec/cmHg, wherein "cc" is the volume of $CO_2$ in cc; "cm²" is the surface area of the polymer in cm²; "mm" is the thickness of the polymer in mm; "sec" is the time in seconds; and "cmHg" is the pressure in cm Hg. The container is then sealed with a seal having a $CO_2$ permeation constant which does not substantially exceed that of the polymer.

The present invention further provides a method of maintaining the pH of an aqueous solution of acyclovir sodium and a method of preventing the precipitation of acyclovir from an aqueous solution of acyclovir sodium, which methods comprises storing aqueous acyclovir sodium according to the present invention.

The invention may best be understood with reference to the accompanying drawings and in the following detailed description of the preferred embodiments.

DESCRIPTION OF THE PREFERRED EMBODIMENTS

Figure 1:
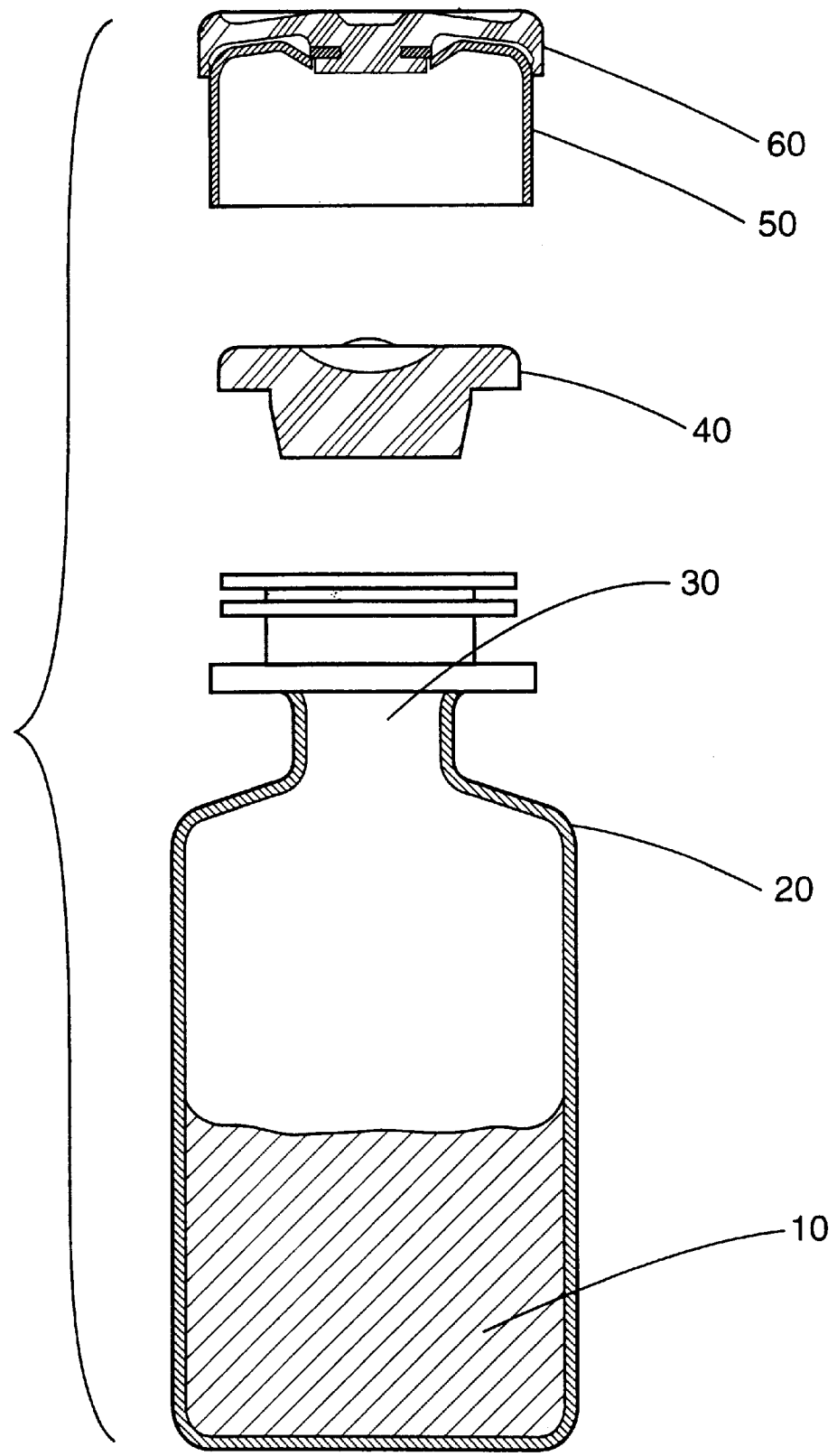
FIG. 1 represents an expanded view of a pharmaceutical product of the present invention.

The present invention provides a pharmaceutical product comprising an aqueous solution of acyclovir sodium contained within a container constructed of an alkali resistant polymer having a $CO_2$ permeation constant of not more than about $3 \times 10^{-8}$ cc/cm²/mm/sec/cmHg, wherein "cc" is the volume of $CO_2$ in cc; "cm²" is the surface area of the polymer in cm²; "mm" is the thickness of the polymer in mm; "sec" is the time in seconds; and "cmHg" is the pressure in cm Hg. The container is sealed with a seal which has a $CO_2$ permeation constant which does not substantially exceed the $CO_2$ permeation constant of the polymer. A preferred embodiment of the present inventive pharmaceutical product is represented by FIG. 1.

The aqueous solution of acyclovir sodium 10 may contain any suitable concentration of acyclovir. Suitable concentrations include, for example, concentrations sufficient to render the acyclovir formulation pharmaceutically acceptable for parenteral administration for a prescribed indication. Preferably, the solution contains at least about 5 mg of acyclovir sodium per mL of solution. More preferably, the solution contains at least about 50 mg of acyclovir sodium per mL of solution. In a preferred embodiment, the concentration of acyclovir sodium is about 54.9 mg/mL, which is equivalent to about 50 mg/mL of the neutral form of acyclovir.

The aqueous acyclovir solution of the present invention can include suitable additives such as, for example, saline, glucose, mannitol, and surfactants. The aqueous acyclovir solution of the present invention may also include suitable co-solvents such as, for example, glycols, polyvinylpyrrolidone, polyvinyl alcohol, ethanol, glycerine, liposomes, or combinations thereof. The aqueous acyclovir solution of the present invention may also include suitable preservatives or buffers.

Preferably, the aqueous solution contains less than about 5% by weight of additives, more preferably less than about 2% by weight of additives, more preferably less than about 1% by weight of additives. Most preferably, the aqueous solution contains no additives. Preferably, the solution contains less than about 10% by weight of a co-solvent, more preferably less than about 5% of a co-solvent by weight. Most preferably, the aqueous solution does not contain a co-solvent. Preferably, the aqueous solution contains less than about 1% preservatives or buffers by weight, and more preferably does not contain preservatives or buffers.

The solution must be maintained at a pH high enough to avoid the formation of a precipitate. While applicants do not wish to be bound to any one particular theory, it is believed that if the pH is too low, the equilibrium concentration in solution will begin to shift in favor of undissociated acyclovir (the neutral form), which is virtually insoluble in water, thereby causing the neutral form to precipitate out of solution. Typically, if a precipitate is readily apparent to the naked eye (e.g., distinct particles), the formulation will not be acceptable for parenteral administration.

It is well known in the art that the pH of an aqueous acyclovir sodium solution depends upon the concentration of acyclovir sodium. The pH of aqueous acyclovir can be calculated using well-established equilibrium principles commonly applied by those of ordinary skill in the art. Acyclovir sodium dissociates to form the anion of acyclovir as expressed in the following equation:

$$AcyNa \leftrightarrows Acy^- + Na^+$$

wherein AcyNa is acyclovir sodium and $Acy^-$ is the dissociated anion of acyclovir. The acyclovir ions interact with water as expressed in the following equation:

$$Acy^- + H_2O \leftrightarrows AcyH + OH^-$$

wherein AcyH is neutral undissociated acyclovir. The concentration of hydroxide ion $[OH^-]$ can be calculated from the equation:

$$X^2/(Y-X) = 10^{-pK_{b2}}$$

wherein X is $[OH^-]$ (which is also equal to [AcyH]), Y is the concentration of $Acy^-$, and $pK_{b2}$ is the $pK_b$ of AcyNa (4.7). The pH of an aqueous acyclovir sodium solution for any concentration Y can be calculated by solving for X in the former equation and applying the following equation:

$$pH = 14 - pOH$$

wherein $pOH = -\log[OH]$. Applying the above principles, the pH for a preferred embodiment having a concentration of 54.9 mg/mL of acyclovir sodium in water (0.222 M) is 11.32, which agrees with the actual value 11.3 as measured by a calibrated pH meter.

For an aqueous acyclovir sodium solution of a given concentration, the pH below which precipitation of neutral acyclovir (AcyH) occurs ($pH_p$) at ambient temperature can be calculated based on the known solubility of AcyH, which is about 1.4 mg/mL (0.0062 M) at ambient temperature, using the following equation:

$$pH_p = pK_{a2} + \log[(Y - 0.0062)/0.0062]$$

wherein $pK_{a2}$ is the pKa for acyclovir sodium (=9.3) and Y−0.0062 is the concentration of $Acy^-$. Applying the foregoing principle, the $pH_p$ for an acyclovir sodium solution having a concentration of 54.9 mg/mL (initial pH 11.3, 0.222 M) is 10.8. Thus, one would expect to begin to see precipitation of a 54.9 mg/mL aqueous acyclovir solution below pH 10.8. This is in agreement with actual observations of 54.9 mg/mL aqueous acyclovir solutions, wherein precipitation becomes apparent at less than about pH 10.8.

It is a critical feature of the present invention that the container 20 is constructed of a polymer which is not only resistant to alkaline attack, but is substantially impermeable to $CO_2$. The term "substantially impermeable" as used herein refers to polymers having a low $CO_2$ permeation constant, preferably having a $CO_2$ permeation constant which is not more than about $3 \times 10^{-8}$ cc/cm$^2$/mm/sec/cmHg. More preferably, the $CO_2$ permeation constant is not more than about $2 \times 10^{-8}$ cc/cm$^2$/mm/sec/cmHg, most preferably not more than about $1 \times 10^{-8}$ cc/cm$^2$/mm/sec/cmHg.

The container can be constructed of any suitable polymer which is substantially impermeable to $CO_2$ such as, for example, polypropylene, Daikyo Resin CZ (sold by Daikyo Gomu Seiko, Ltd., reported in some references as polymethylpentene) and polyethylene terephthalate. In a preferred embodiment, the polymer of which the container is constructed is polypropylene.

Many standard plastics do not provide an adequate carbon dioxide ($CO_2$) barrier, which has now been discovered to be critical to the stability and shelf life of aqueous acyclovir sodium solutions. Even if the plastic does not degrade chemically under alkaline conditions, the permeation of $CO_2$ through the container material and into the acyclovir solution has been found to result in a decrease in pH and the formation of a precipitate, which renders the solution unsuitable for parenteral administration. The presence of atmospheric carbon dioxide makes it virtually impossible to avoid the detrimental effect of $CO_2$ upon aqueous acyclovir sodium in the absence of an adequate $CO_2$ barrier.

In a preferred manufacturing process, the acyclovir solution preparation and filling processes are performed in the absence of ambient $CO_2$. Since $CO_2$ is naturally present under ambient atmospheric conditions, contact with $CO_2$ can be avoided by purging the components of the formulation (e.g., the solvent and final formulation), filling equipment, and containers with an inert gas, such as, for example, nitrogen or argon. Typically, the solvent is purged with nitrogen and the solution is prepared under a nitrogen purge to prevent $CO_2$ influx. The containers and filling equipment are purged with nitrogen prior to filling. All transferring and filling processes are performed under a nitrogen atmosphere prior to sealing the containers. The filling of containers under a nitrogen purge prevents ambient $CO_2$ from entering the container head space (the unfilled gaseous atmosphere above the liquid level in the container). The formulation, equipment, and containers are sterilized, and all operations are conducted under sterile conditions. When the manufacturing process is conducted under a nitrogen atmosphere, the initial pH of the acyclovir sodium solution (at the time of manufacture) typically agrees with the theoretical pH, whereas product preparation under normal atmospheric conditions (without purging) typically results in a solution pH below the theoretical pH. Since shelf life is a function of pH, it is preferred to manufacture the product in the absence of $CO_2$.

The container is provided with an opening 30 and a means for sealing the opening such that the sealed container is substantially impermeable to $CO_2$. It is preferred that the means for sealing the container comprises a material having a $CO_2$ permeation constant which does not substantially exceed the $CO_2$ permeation constant of the polymer. By the term "substantially exceed" is meant that the $CO_2$ permeation constant of the means for sealing the container does not exceed the $CO_2$ permeation constant of the polymer of which the container is constructed by more than about 20%. The means for sealing the opening can have greater thickness and far less surface area than the polymer of which the container is constructed. Since the permeation of $CO_2$ is inversely proportional to thickness and directly proportional to surface area, the means for sealing the container can form a suitable $CO_2$ barrier, even though it may have a higher permeation constant than that of the polymer of which the container is constructed. A suitable means for sealing the container includes, for example, a stopper, cap, lid, closure, or covering which fluidly seals the container such that gasses will not enter the aqueous formulation through the opening of the container. Examples of suitable closures for medical vials can be found in U.S. Pat. No. 4,671,331 and references cited therein. The means for sealing the container of the present invention is not limited to separate closures or closure devices, but also includes self-sealing containers and containers which are manufactured and sealed during filling operations. Accordingly, the containers used in the present invention may be manufactured according to well known Form-Fill-Seal technology, such as that described in U.S. Pat. Nos. 5,500,067, 4,807,420, or 4,178,976. Alteratively, containers such as prefilled syringes may be used, as described in U.S. Pat. No. 5,620,425.

Preferably, the means for sealing the container comprises a material which has a $CO_2$ permeation constant no greater than the $CO_2$ permeation constant of the polymer of which the container is constructed. More preferably, the means for sealing the container has a lower $CO_2$ permeation constant than that of the polymer of which the container is constructed. Most preferably, the means for sealing the container is impermeable to $CO_2$.

In a preferred embodiment, the opening 30 of the container is fitted with a stopper 40 configured to fluidly seal the opening. Any suitable stopper can be used. Suitable stoppers include conventional medical grade stoppers which do not degrade or release significant impurities upon exposure to the alkaline environment of the aqueous acyclovir solution. Preferably, the stopper is constructed of an elastomer, which is more preferably an elastomer which is pierceable by a hypodermic needle or a blunt cannula. In one preferred embodiment, the stopper is a Gray Teflon-faced stopper marketed by The West Company. In another preferred embodiment, the stopper is a 6720GC Gray Rubber Stopper form American Stelmi Corporation.

Optionally, an outer seal 50 is provided which covers and entirely surrounds the stopper 40. The seal can be constructed of any suitable material. Although an outer seal is optionally provided, the outer seal need not be a good barrier toward $CO_2$ influx. However, if desired, the outer seal may be used as an additional $CO_2$ barrier which further prevents influx of external $CO_2$ into opening 30. In a preferred embodiment, the seal is fitted with a lid 60 which can be easily manually removed, thereby providing access to the stopper. Preferably, the seal, 50 and 60, is a Flip-off Aluminum/Polypropylene Seal (lacquered or non-lacquered aluminum), marketed by The West Company, Inc., and other manufacturers.

The present invention further provides a pharmaceutical product with a shelf life of at least about 18 months comprising an aqueous solution of acyclovir sodium, of predetermined volume and concentration, such that the pH of the solution due to $CO_2$ permeation does not fall below the pH of precipitation ($pH_p$) for at least about 18 months. Preferably, the shelf life of the solution in the sealed container is at least about 24 months.

It has been discovered that the shelf life of aqueous acyclovir sodium can be substantially prolonged by avoiding contact with $CO_2$. As indicated earlier, the pH of aqueous acyclovir sodium must be maintained above the $pH_p$ to avoid the formation of precipitates. Haziness has been observed to occur in solutions containing about 55 mg/mL of acyclovir sodium when the solution drops below about pH 10.8, which is the theoretical $pH_p$ for a 54.9 mg/mL aqueous solution of acyclovir sodium. While the applicant does not wish to be bound by any particular theory, it is believed that acidification occurs in an aqueous solution as a result of contact with $CO_2$ due to the reaction of $CO_2$ with water to form carbonic acid ($H_2CO_3$), which lowers the pH sufficiently to result in the formation of the neutral form of acyclovir, which precipitates out of solution due to its poor water solubility. The solubility of acyclovir sodium in water is approximately 644 mg/mL, whereas the solubility of the neutral form is significantly lower (approximately 1.4 mg/mL).

The presence of $CO_2$ in the atmosphere makes it practically impossible to avoid contact with $CO_2$ if the container is to be stored under normal atmospheric conditions. The present pharmaceutical product utilizes a container constructed of a material, preferably polypropylene, which is not only resistant to alkaline attack, but also provides a barrier toward external $CO_2$, significantly increasing the shelf life of aqueous acyclovir formulation. The $CO_2$ permeation constant of polypropylene has been reported in at least two sources. In D&CI/March, p. 156 (1968), the $CO_2$ permeation constant of polypropylene is reported as $92 \times 10^{-10}$ cc/cm²/mm/sec/cmHg, while Mod. Plastic Encyclopedia, 47–48 (10A)(1970–1972) reports a somewhat lower value of $27 \times 10^{-10}$ cc/cm²/mm/sec/cmHg. The shelf life of the aqueous acyclovir solution can be increased by increasing the wall thickness of the container to provide a barrier with increased resistance to $CO_2$ permeation. Preferably, the average wall thickness of the container is greater than about 0.3 mm, more preferably greater than about 0.5 mm, most preferably, greater than about 0.9 mm. In general, the shelf life of a particular aqueous acyclovir solution increases with increasing wall thickness of the container due to less total molar $CO_2$ permeation over time.

Of course, it is within the scope of the present invention to provide an outer container of a suitable material, such as glass or a suitable polymer, or a pouch, in addition to the container in which the acyclovir sodium solution is stored to prevent influx of $CO_2$. Indeed, any suitable additional means for preventing the influx of $CO_2$ is deemed within the scope of the present invention.

The present invention is further directed to a method of storing an aqueous solution of acyclovir sodium, wherein a predetermined volume and concentration of an aqueous solution of acyclovir sodium is stored in the sealed container of the present invention. The container is provided with an opening and a means for sealing the opening such that the sealed container is substantially impermeable to $CO_2$. The means for sealing the container includes any suitable means, including a stopper and optional seal as defined herein. An aqueous solution of acyclovir sodium is placed in the container and the container is sealed to provide a container having a $CO_2$ permeation constant of not more than about $3 \times 10^{-8}$ cc/cm²/mm/sec/cmHg. The acyclovir sodium solution may be derived from any suitable source. The acyclovir sodium solution of the present invention need not be lyophilized since reconstitution of the acyclovir sodium is not necessary in the pharmaceutical products or methods of the present invention. Sterile solutions to be utilized under the present method can be obtained by any suitable means, including, for example, filtration through a suitable membrane. Any suitable concentration of acyclovir can be stored under the present inventive method. In a preferred embodiment, the concentration of acyclovir sodium is about 55 mg/mL of acyclovir sodium. It is preferred that the container is made of a polymer having a $CO_2$ permeation constant of not more than about $3 \times 10^{-8}$ cc/cm²/mm/sec/ cmHg, more preferably not more than $1 \times 10^{-8}$ cc/cm²/mm/ sec/cmHg. In a preferred embodiment, the container is constructed of polypropylene.

The present invention is further directed to a method of maintaining the pH of an aqueous solution of acyclovir sodium wherein the aqueous solution of acyclovir sodium is stored in a sealed container according to the present method. The present invention is further directed to a method of preventing the precipitation of acyclovir from an aqueous solution of acyclovir sodium wherein the aqueous solution of acyclovir sodium is stored according to the present method.

In one preferred embodiment, the present invention provides a pharmaceutical product comprising an aqueous solution of acyclovir sodium within a sealed container, wherein the sealed container has a $CO_2$ permeation rate per mL of acyclovir solution of not more than about $2.6 \times 10^{-3}$ cc of $CO_2$ per mL of acyclovir per month of storage under normal atmospheric conditions. By the term "normal atmospheric conditions" is meant that the atmospheric pressure as well as the pressure in the container is about 1 atm, and the atmospheric $CO_2$ concentration is about 0.033% to about 0.1% by volume. It is assumed that the $CO_2$ is consumed immediately and that the $CO_2$ concentration in the container is zero as a result thereof. It would be readily apparent to a person of ordinary skill in the art that the shelf life of aqueous acyclovir sodium, as measured by the amount of $CO_2$ permeation required to cause the solution to reach the $pH_p$, depends on several variables such as, for example, the polymer used in the container, the surface area and thickness of the polymer, the concentration of acyclovir sodium (which effects the $pH_p$), and the volume of solution in the container. An acyclovir sodium solution of very high concentration would have a shorter shelf life than a solution of equal volume, but lower concentration of acyclovir sodium, if both were stored in the same container under normal atmospheric conditions, due to the differences in $pH_p$. If two acyclovir sodium solutions of equal concentration were stored in the same container under normal atmospheric conditions, but were of different volumes, the solution of lower volume would have a shorter shelf life because less volume (or molar quantity) of $CO_2$ is required to cause the pH of the lower volume solution to drop below the $pH_p$.

Of course, the shelf life of two identical acyclovir sodium solutions under identical conditions also depends on the nature of the container, including, for example, the $CO_2$ permeation constant of the polymer, polymer thickness and polymer surface area. For an aqueous acyclovir sodium solution having a concentration of 54.9 mg/mL, the sealed container should have a $CO_2$ permeation rate such that the volume of $CO_2$ permeated per mL of acyclovir sodium solution is not more than about $2.6 \times 10^{-3}$ cc of $CO_2$ per mL of acyclovir sodium solution per month of storage under normal atmospheric conditions to obtain a shelf life greater than about 18 months.

In a preferred embodiment, the pharmaceutical product of the present invention comprises a container having a $CO_2$ permeation rate of not more than about $2.0 \times 10^{-3}$ cc per mL acyclovir sodium solution per month of storage under normal atmospheric conditions. More preferably, the pharmaceutical product of the present invention comprises a container having a $CO_2$ permeation rate of not more than about $1.5 \times 10^{-3}$ cc per mL acyclovir sodium solution per month of storage under normal atmospheric conditions.

The following examples further illustrate the present invention but, of course, should not be construed as in any way limiting its scope.

EXAMPLE 1

This example represents the effect of $CO_2$ on the pH of an unbuffered aqueous sodium hydroxide solution. An aqueous solution of sodium hydroxide of pH 11.31 was prepared from nitrogen-purged purified water to simulate an aqueous acyclovir solution having a pH of 11.3 at the time of manufacture. The solution was placed in a series of identical polypropylene vials which were sealed and separated into two groups (Groups A and B). The vials were identical in every relevant parameter, including average wall thickness, surface area, and stoppers. The sodium hydroxide solution in all samples were taken from the same lot and each vial was filled under identical filling conditions. Samples in group A were stored under normal atmospheric conditions. Samples in group B were placed in a 5.8 L desiccator along with a beaker containing 50 mL of 1N aq. HCl (0.05 moles HCl). After carefully adding 100 mL of 0.5M $NaHCO_3$ (0.05 moles $NaHCO_3$) to the HCl solution, the desiccator was immediately sealed to prevent further escape of the resulting $CO_2$ (approximately 0.05 moles $CO_2$). The calculated concentration of $CO_2$ in the chamber was approximately 18% by volume. The samples were allowed to stand for 3 weeks under the aforesaid conditions. The pH of the samples in the containers was measured using a calibrated standard pH meter. The results are shown in Table 1.

TABLE 1

| Atmospheric | pH | | |
| --- | --- | --- | --- |
| Conditions | Initial | 1 Week | 3 Weeks |
| Group A Normal Atmosphere | 11.31 | 11.22 | 11.21 |
| Group B $CO_2$ Chamber (approx. 18% $CO_2$ by vol.) | 11.31 | — | 6.37 |

These results demonstrate that the presence of external $CO_2$ has a substantial effect upon the pH of alkaline solutions as evidenced by the significant pH drop in Group B after 3 weeks in the $CO_2$ chamber.

EXAMPLE 2

This example demonstrates the stability of aqueous acyclovir sodium solutions stored in the sealed container of the present invention under various accelerated $CO_2$ permeation conditions. A sterile solution of aqueous acyclovir having a concentration of 54.9 mg of acyclovir sodium per mL of solution (54.9 mg/mL) was prepared by the following procedure. All equipment which came in direct contact with the acyclovir solution was autoclaved at 121° C. for 45 minutes. 574.88 g of acyclovir sodium, manufactured by Heumann Pharma GmbH, was weighed and transferred into a 20 L stainless steel vessel. The weight of acyclovir was corrected for water content. Nitrogen-purged purified water was added with stirring to give 10 L of an aqueous acyclovir solution. The resulting solution had a concentration of 54.9 mg per mL of solution and a density of 1.024 g/mL. The solution was transferred, under a nitrogen atmosphere, to autoclaved filling equipment contained within a laminar air-flow hood to avoid particle and microbiological contamination. The bulk solution was filtered through a sterilized 0.22 μm Ultipore sterile Nylon 66 filter and prefilter assembly. The filtered bulk solution was transferred into polypropylene vials (Rexene Resin 23 M2-CS38) from Owens-Brockway which were washed with 0.45 μm filtered purified water, steam sterilized, and purged with nitrogen in a laminar air-flow hood. The vials were immediately sealed using sterilized 6720GC Gray Rubber Stopper from American Stelmi Corp. and crimped with Flip-off Aluminum/Polypropylene Seals (Laquer) from The West Company. The filtered bulk solution and containers were purged with nitrogen during the filling process to avoid $CO_2$ absorption. The process was repeated for polyethylene terephthalate vials and Daikyo Resin CZ vials (sold by Daikyo Gomu Seiko, Ltd, reported in some references as polymethylpentene).

The samples were tested under accelerated $CO_2$ storage conditions. The samples were placed in three different chambers with elevated $CO_2$ atmospheres, maintained at a concentration of approximately 2%, 5%, and 10% $CO_2$ by volume, for 3 weeks. The pH was measured at various times using a calibrated standard pH meter. The results are shown in Table 2. After 3 weeks, no precipitate was observed.

TABLE 2

| $CO_2$ Conc. (% by vol.) | Vial Polymer | Fill Volume (mL) | Initial pH | pH After 1 Week | pH After 2 Weeks | pH After 3.5 Weeks |
| --- | --- | --- | --- | --- | --- | --- |
| 2% | Polypropylene | 50 | 11.30 | 11.29 | 11.19 | 11.12 |
|  | Polyethylene Terephthalate | 20 | 11.30 | 11.30 | 11.26 | 11.22 |
| 5% | Polypropylene | 50 | 11.30 | 11.25 | 11.07 | 10.97 |
|  | Polyethylene Terephthalate | 20 | 11.30 | 11.33 | 11.24 | 11.22 |
| 10% | Polypropylene | 50 | 11.30 | 11.17 | 10.93 | 10.82 |
|  | Polyethylene Terephthalate | 50 | 11.30 | 11.30 | 11.23 | 11.06 |
|  | Daikyo CZ Resin | 20 | 11.30 | 11.21 | 10.95 | 10.80 |

These results demonstrate that aqueous acyclovir sodium can be maintained at a high pH despite the presence of a considerable external $CO_2$ challenge. Although the rate of pH decline is slightly more rapid with increasing $CO_2$ concentration (0.33 pH units after 3 weeks at a $CO_2$ concentration of 5% vs. 0.48 pH units after 3 weeks at a $CO_2$ concentration of 10%), the solutions remained sufficiently alkaline to prevent the formation of precipitates.

EXAMPLE 3

This example illustrates the compatibility of acyclovir sodium with the container and seal materials of the present pharmaceutical product. A solution of aqueous acyclovir was prepared and the solution placed in polypropylene vials and sealed in accordance with Example 2, except the vials were stoppered using sterilized 4416/50 Teflon® coated stoppers from The West Co. The sealed vials were stored under normal atmospheric conditions at room temperature (R.T.) and at 40° C. for three months in both inverted (upside down) and upright orientation. At various time intervals, the samples were tested for pH. The pH was measured using a calibrated standard pH meter. The pH results are shown in Table 3

TABLE 3

| Storage Temp. (° C.) | Interval (months) | Orientation ↑ (upright) ↓ (inverted) | pH |
|---|---|---|---|
| RT | 0 | ↑ | 11.25 |
|  | 2 | ↑ | 11.21 |
|  |  | ↓ | 11.20 |
|  | 3 | ↑ | 11.21 |
|  |  | ↓ | 11.21 |
| 40° C. | 1 | ↑ | 11.13 |
|  |  | ↓ | 11.13 |
|  | 2 | ↑ | 11.05 |
|  |  | ↓ | 11.05 |
|  | 3 | ↑ | 11.00 |
|  |  | ↓ | 11.00 |

These data demonstrate that aqueous acyclovir is compatible with the materials used in the container and stopper. The orientation did not appear to affect solution compatibility. Further, HPLC analysis confirmed that no significant impurities were generated. In agreement with theory, no precipitation was observed upon visual inspection.

EXAMPLE 4

This example illustrates the prediction of the shelf life of aqueous acyclovir in polypropylene vials. The shelf life was predicted by calculation, under Fick's diffusion law, of the time required for a sufficient quantity of $CO_2$ to permeate through the polypropylene vials under normal atmospheric conditions to cause the pH to drop below 10.8, the pH below which acyclovir theoretically begins to precipitate as the undissociated neutral form.

The following values were assigned in the calculation:

| | |
|---|---|
| Permeation constant of polypropylene | $92 \times 10^{-10}$ cc/cm²/mm/sec/cmHg (the higher reported value) |
| Surface area of container | 10 mL vial: 33 cm² |
|  | 20 mL vial: 47 cm² |
|  | 50 mL vial: 82 cm² |
| Wall thickness of container | average measurement (mm, as indicated) |
| Atmospheric $CO_2$ concentration | 0.033 ± 0.001% by volume (CRC Handbook of Chem.&Phys., 65th Ed.) |
| Acyclovir sodium | MW = 247.21 |
|  | $pK_{a2}$ = 9.3 |
|  | $pK_{b2}$ = 4.7 |
|  | aqueous solubility = 643.82 mg/mL (determined experimentally) |
| Acyclovir (neutral) | aqueous solubility = 1.4 mg/mL (0.00620 M) |
| Carbonic acid | (Pharm. Res., vol. 8, p. 1087 (1991)) |
|  | $pK_{a1}$ = 6.35 |
|  | $pK_{a2}$ = 10.25 |
| Aqueous solution used in calculations | conc. of acyclovir sodium = 54.9 mg/mL theoretical pH = 11.32 actual measured pH = 11.3 |
| Atmospheric pressure | 76 cmHg |
| Temperature | 298.15 K |

In the calculation, it is assumed that the diffusion of $CO_2$ through the plastic vial is rate limiting (i.e., each molecule of $H_2CO_3$ forms two molecules of neutral acyclovir). It is also assumed that the $CO_2$ which permeates into the head space (atmosphere in vial above the liquid level) is consumed instantaneously, thereby maintaining zero concentration of $CO_2$ in the head space.

The calculation was based on an aqueous solution of 54.9 mg of acyclovir sodium per mL of water (0.222 M), without additional ingredients, such as buffers and co-solvents. The volume of aqueous acyclovir sodium used in each of the vials is the actual fill volume for the vials used in the present invention. The fill volume for the 10 mL vials is 10 mL of solution, the fill volume for the 20 mL vials is 20 mL of solution, and the fill volume for the 50 mL vials is 50 mL of solution.

The volume of $CO_2$ which permeates through the vial per month was calculated using the following equation:

$$V = PSC_d t/h$$

where P=permeation constant of polypropylene in cc/cm²/mm/sec/cmHg; S=surface area of vial in cm², $C_d$=pressure difference of $CO_2$ (0.00033×76 cmHg), t=time in seconds per month, and h=container thickness in mm. The moles of $CO_2$ were calculated using the ideal gas law equation (PV=nRT). The pH change with respect to time due to permeation of $CO_2$ was calculated using the following equation:

$$pH = pK_a + \log([X]/[Y])$$

where [X]=concentration of acyclovir ion, and [Y]=concentration of acyclovir neutral form. The pH at various time points was calculated for five vials of different surface area and average wall thickness. The results are shown in Table 4.

TABLE 4

| | pH 50 mL vials (S = 82 cm²) | | pH 20 mL vials (S = 47 cm²) | | pH 10 mL vials (S = 33 cm²) | |
|---|---|---|---|---|---|---|
| Time Interval (months) | (h = 0.98 mm) | (h = 0.38 mm) | (h = 0.38 mm) | (h = 0.54 mm) | (h = 0.38 mm) | (h = 0.63 mm) |
| 0 | — | 11.30 | 11.30 | 11.30 | 11.30 | 11.30 |
| 2 | — | 11.21 | 11.19 | 11.21 | 11.16 | 11.20 |
| 4 | — | 11.16 | 11.11 | 11.16 | 11.05 | 11.13 |
| 6 | — | 11.10 | 11.03 | 11.10 | 10.97 | 11.07 |
| 8 | — | 11.05 | 10.97 | 11.05 | 10.89 | 11.01 |
| 10 | — | 11.00 | 10.92 | 11.00 | 10.83 | 10.96 |
| 12 | — | 10.96 | 10.87 | 10.96 | 10.77 | 10.91 |
| 14 | — | 10.92 | 10.83 | 10.92 | 10.73 | 10.87 |
| 16 | — | 10.89 | 10.79 | 10.89 |  | 10.83 |
| 18 | — | 10.86 | 10.75 | 10.86 |  | 10.80 |

TABLE 4-continued

| | pH 50 mL vials (S = 82 cm²) | | pH 20 mL vials (S = 47 cm²) | | pH 10 mL vials (S = 33 cm²) | |
|---|---|---|---|---|---|---|
| Time Interval (months) | (h = 0.98 mm) | (h = 0.38 mm) | (h = 0.38 mm) | (h = 0.54 mm) | (h = 0.38 mm) | (h = 0.63 mm) |
| 20 | — | 10.83 | | 10.83 | | 10.77 |
| 22 | — | 10.80 | | 10.80 | | |
| 24 | 11.02 | 10.77 | | 10.77 | | |

The calculated pH values demonstrate the predicted shelf lives of aqueous acyclovir for vials of different surface areas and wall thickness. Based on the above calculations, a 50 mL polypropylene vial of the present pharmaceutical product with a wall thickness of 0.98 mm would have a pH of approximately 11.0 and an expected shelf life in excess of two years.

EXAMPLE 5

The pH at which precipiation begins to occur ($pH_p$) for aqueous acyclovir sodium solutions at various concentrations was calculated. The initial concentration and pH value for each solution was calculated based on the pH at the time of manufacture under nitrogen purging conditions (no $CO_2$ present in the filling process or container head space). The concentration in mg/mL is shown in mg of undissociated acyclovir (neutral AcyH, MW=225.19, $pK_a$=9.3) per mL of water. The results are shown in Table 5.

TABLE 5

| Conc. (mg AcyH/mL) | Conc. (M) | [OH⁻] (M) | pOH | pH (initial) | $pH_p$ |
|---|---|---|---|---|---|
| 50 | 0.222 | 2.10 × 10⁻³ | 2.68 | 11.32 | 10.84 |
| 45 | 0.200 | 1.99 × 10⁻³ | 2.70 | 11.30 | 10.79 |
| 40 | 0.178 | 1.88 × 10⁻³ | 2.73 | 11.27 | 10.74 |
| 35 | 0.155 | 1.75 × 10⁻³ | 2.76 | 11.24 | 10.68 |
| 30 | 0.133 | 1.62 × 10⁻³ | 2.79 | 11.21 | 10.61 |
| 25 | 0.111 | 1.48 × 10⁻³ | 2.83 | 11.17 | 10.53 |
| 20 | 0.089 | 1.32 × 10⁻³ | 2.88 | 11.12 | 10.42 |
| 15 | 0.067 | 1.14 × 10⁻³ | 2.94 | 11.06 | 10.29 |
| 10 | 0.044 | 9.32 × 10⁻⁴ | 3.03 | 10.97 | 10.09 |
| 5 | 0.022 | 6.56 × 10⁻⁴ | 3.18 | 10.81 | 9.71 |

These data demonstrate the relationship between $pH_p$ and initial concentration of acyclovir sodium. The $pH_p$ decreases with decreasing initial concentration of acyclovir sodium, and the difference between the initial pH and the $pH_p$ increases with decreasing initial concentration of acyclovir sodium. These data can be used to predict shelf life of aqueous acyclovir sodium at various concentrations in a particular container of the present invention. These data can further be used toward the design of container parameters, such as container thickness and surface area for a polymer having a particular $CO_2$ permeability constant, to achieve a desired shelf life for a particular concentration of aqueous acyclovir.

EXAMPLE 6

This example demonstrates the effect of $CO_2$ on the pH of an aqueous acyclovir solution in the container of the present invention under accelerated pH conditions and confirms the permeability constant for the vial polymer (polypropylene). A solution of 54.9 mg/mL of acyclovir sodium in nitrogen-purged purified water was prepared without purging the vial headspace with nitrogen. The solution was placed in two different sized vials: 10 mL Rexene Polypropylene vials, Lot #106–1225 (Rexene Resin No. 23 M2-CS38, fill volume=10 mL, surface area=33 cm², ave. thickness=0.71 mm); and 20 mL Rexene Polypropylene vials, Lot #21-B (Rexene Resin No. 23 M2-CS38, fill volume=20 mL, surface area=47 cm², ave. thickness=0.51 mm). The $pH_p$ for a 54.9 mg/mL of acyclovir sodium in purified water is 10.8 and the initial pH of the solution in the absence of $CO_2$ (i.e., with purging headspace) is 11.3.

Half of the sample vials were stored in a sealed desiccator with an atmospheric $CO_2$ concentration maintained at 2.00%, and the other half were stored in a sealed desiccator with an atmospheric $CO_2$ concentration of 10.1%. The $CO_2$ atmosphere for each desiccator was created by filling with Great Lakes Airgas 2.00% $CO_2$ Primary Standard (for the 2.00% atmosphere) and Great Lakes Airgas 10.1% $CO_2$ Primary Standard (for the 10.1% atmosphere). The desiccators were evacuated and filled with the $CO_2$ standards three consecutive times at the beginning of the experiment, and the filling process was repeated each week and each time the desiccators were opened for removing samples. The pressure in the desiccators was maintained at 1 atm. The pH was measured at various time intervals. The volume of $CO_2$ was calculated based on the moles of $CO_2$ required to cause the measured drop in pH of the acyclovir solutions. The results are shown in Table 6a.

TABLE 6a

| | 2.00% $CO_2$ Atmosphere | | | | 10.1% $CO_2$ Atmosphere | | | |
|---|---|---|---|---|---|---|---|---|
| | 10 mL vials | | 20 mL vials | | 10 mL vials | | 20 mL vials | |
| Days | Measured pH | $CO_2$ Vol. (cc) | Measured pH | $CO_2$ Vol. (cc) | Measured pH | $CO_2$ Vol. (cc) | Measured pH | $CO_2$ Vol. (cc) |
| 0 | 11.24 | 0.100 | 11.25 | 0.175 | 11.24 | 0.100 | 11.25 | 0.175 |
| 2 | 11.23 | 0.113 | 11.23 | 0.226 | 11.15 | 0.218 | 11.15 | 0.437 |

TABLE 6a-continued

| | 2.00% $CO_2$ Atmosphere | | | | 10.1% $CO_2$ Atmosphere | | | |
|---|---|---|---|---|---|---|---|---|
| | 10 mL vials | | 20 mL vials | | 10 mL vials | | 20 mL vials | |
| Days | Measured pH | $CO_2$ Vol. (cc) | Measured pH | $CO_2$ Vol. (cc) | Measured pH | $CO_2$ Vol. (cc) | Measured pH | $CO_2$ Vol. (cc) |
| 6 | 11.18 | 0.178 | 11.19 | 0.330 | 10.94 | 0.553 | 10.97 | 0.997 |
| 9 | 11.18 | 0.178 | 11.17 | 0.383 | 10.87 | 0.696 | 10.90 | 1.26 |
| 14 | 11.10 | 0.289 | 11.12 | 0.521 | 10.70 | | 10.74 | |
| 16 | 11.08 | 0.319 | 11.10 | 0.578 | N/A | | N/A | |
| 20 | 11.03 | 0.396 | 11.07 | 0.667 | N/A | | N/A | |
| 23 | 11.03 | 0.396 | 11.05 | 0.729 | N/A | | N/A | |
| 27 | 11.01 | | 11.02 | | N/A | | N/A | |

The permeability constant for polypropylene was obtained by applying the following equation:

$$p = (\Delta M)(L/S)[(P_1)(\Delta t)]^{-1}$$

wherein p=permeability constant ([(cc)(mm)]/[(cm²)(sec)(cmHg)]), M=volume of carbon dioxide permeating through the vial (cc), L=vial thickness (mm), S=surface area (cm²), $P_1$=carbon dioxide pressure outside the vial (cm Hg), and t=time (sec). The internal $CO_2$ pressure is assumed to be zero). The relationship of volume of $CO_2$ permeated as a function of time was linear. The average values for the permeability constant for polypropylene as calculated based on measured pH drop are shown in Table 6b.

TABLE 6b

| Vial Size (mL) | Storage Conditions | Slope ($\Delta M/\Delta t$) × $10^7$ | Correlation Coefficient | Wall Thickness (mm) | Surface Area (cm²) | Permeability Constant[1] × $10^{-10}$ |
|---|---|---|---|---|---|---|
| 10 | 2.00% $CO_2$ | 1.64 | 0.987 | 0.71 | 33 | 23.6 |
| | 10.1% $CO_2$ | 7.96 | 0.994 | 0.71 | 33 | 22.8 |
| 20 | 2.00% $CO_2$ | 2.82 | 0.999 | 0.51 | 47 | 20.5 |
| | 10.1% $CO_2$ | 14.3 | 0.996 | 0.51 | 47 | 20.7 |

[1][(cc) (mm)]/[(cm²) (sec) (cmHg)]

These data demonstrate that the pH drop over time is a function of $CO_2$ permeability. The $CO_2$ permeability constant for polypropylene as calculated by the measured pH is in agreement with the lower reported constant of $27 \times 10^{-10}$ (cc)(mm)]/[(cm²)(sec)(cmHg) for polypropylene. The agreement between the reported permeability constant for polypropylene and the permeability constant based on experimentally measured pH demonstrates that the actual shelf life of aqueous acyclovir can be accurately predicted based on the calculations disclosed herein.

EXAMPLE 7

Using the permeability constant calculated for the 10 mL vial under 2.00% $CO_2$ storage conditions in Example 6, the pH as a function of time for a 54.9 mg/mL aqueous acyclovir solution was calculated based on normal atmospheric storage conditions. The calculation was based on a starting pH of 11.32, which is the initial pH for the solution filled under a nitrogen purge. The $pH_p$ is 10.8. The atmospheric $CO_2$ content, measured using a Dickson, Model $CO_2X$ carbon dioxide recorder, was measured as 0.07% by volume and this value was used in the calculation. The vial parameters are shown in Example 6. The results for the 10 mL vial are shown in Table 7.

TABLE 7

| Time (Months) | $CO_2$ Volume (cc) | pH |
|---|---|---|
| 0 | 0 | 11.32 |
| 3 | 0.0454 | 11.28 |
| 6 | 0.0908 | 11.25 |
| 9 | 0.136 | 11.21 |
| 12 | 0.182 | 11.18 |
| 18 | 0.272 | 11.11 |
| 24 | 0.363 | 11.05 |

This example demonstrates that the shelf life of aqueous acyclovir stored according to the present invention is greater than 24 months. After 24 months, the pH of the formulation would be greater than the $pH_p$ for acyclovir sodium.

EXAMPLE 8

Using the permeability constant calculated for the 20 mL vial under 2.00% $CO_2$ storage conditions in Example 6, the pH as a function of time for a 54.9 mg/mL aqueous acyclovir solution was calculated based on normal atmospheric storage conditions. The calculation was based on a starting pH of 11.32, which is the initial pH for the solution filled under a nitrogen purge. The $pH_p$ is 10.8. The atmospheric $CO_2$ content, measured using a Dickson, Model $CO_2X$ carbon dioxide recorder, was measured as 0.07% by volume and this value was used in the calculation. The vial parameters are shown in Example 6. The results for the 20 mL vial are shown in Table 8.

TABLE 8

| Time (Months) | $CO_2$ Volume (cc) | pH |
|---|---|---|
| 0 | 0 | 11.32 |
| 3 | 0.0781 | 11.29 |
| 6 | 0.156 | 11.26 |
| 9 | 0.234 | 11.23 |
| 12 | 0.313 | 11.20 |
| 18 | 0.469 | 11.14 |
| 24 | 0.625 | 11.08 |

This example demonstrates that the shelf life of aqueous acyclovir stored according to the present invention is greater than 24 months. After 24 months, the pH of the formulation would be greater than the $pH_p$ for acyclovir sodium.

EXAMPLE 9

This example illustrates the measured pH drop over 21 months of aqueous acyclovir sodium under normal atmospheric conditions. Two solutions containing 54.9 mg/mL of acyclovir in water were prepared according to Example 2. One lot was placed in 10 mL Rexene polypropylene vials (fill volume=10 mL, surface area=33 cm², ave. thickness= 0.71 mm, stopper: Stelmi 6720 GC, 20 mm) and the other lot was placed in 20 mL Rexene polypropylene vials, (fill volume=20 mL, surface area=47 cm², ave. thickness=0.51 mm, stopper: Stelmi 6720 GC, 20 mm). For each vial, one half was stored in the upright position and the other half was stored in the inverted position. The pH was measured over time using a standard calibrated pH meter. The results are shown in Table 9.

TABLE 9

| Time | pH (measured) | | | |
|---|---|---|---|---|
| | 10 mL Vials | | 20 mL Vials | |
| (Months) | Upright | Inverted | Upright | Inverted |
| 0 | 11.37 | 11.37 | 11.37 | 11.37 |
| 3 | 11.30 | 11.31 | 11.32 | 11.31 |
| 6 | 11.27 | 11.27 | 11.28 | 11.27 |
| 9 | 11.13 | 11.13 | 11.16 | 11.14 |
| 12 | 11.09 | 11.09 | 11.11 | 11.10 |
| 18 | 10.99 | 10.99 | 10.98 | 10.97 |
| 21 | 11.00 | 11.00 | 11.03 | 11.02 |

These data demonstrate, in real time, that the shelf life of an aqueous acyclovir solution stored according to the present invention is 21 months or greater. These results are in agreement with theory. After 21 months, the pH of the formulation stayed above the $pH_p$ for acyclovir sodium and no precipitates were detected. Acyclovir sodium solutions stored according to the present invention remained acceptable for parenteral administration for at least 21 months of storage under normal atmospheric conditions, whether stored in the upright or inverted position.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A pharmaceutical product comprising an aqueous solution of acyclovir sodium within a container, wherein said container is constructed of a polymer having a $CO_2$ permeation constant of not more than about $1 \times 10^{-8}$ cc/cm²/mm/sec/cmHg, said container defining an opening, and a means for sealing said opening to provide a sealed container with a $CO_2$ permeation constant of not more than about $1 \times 10^{-8}$ cc/cm²/mm/sec/cmHg.

2. The pharmaceutical product of claim 1, wherein said aqueous solution of acyclovir sodium comprises not less than about 5 mg/mL of acyclovir sodium.

3. The pharmaceutical product of claim 1, wherein said aqueous solution of acyclovir sodium comprises not less than about 50 mg/mL of acyclovir sodium.

4. The pharmaceutical product of claim 1, wherein the initial pH of said aqueous solution of acyclovir sodium, at the time of preparation under an inert atmosphere, is not less than about 10.8.

5. The pharmaceutical product of claim 1, wherein the initial pH of said aqueous solution of acyclovir sodium, at the time of preparation under an inert atmosphere, is not less than about 11.0.

6. The pharmaceutical product of claim 1, wherein the initial pH of said aqueous solution of acyclovir sodium, at the time of preparation under an inert atmosphere, is not less than about 11.3.

7. The pharmaceutical product of claim 1, wherein aid polymer comprises polypropylene.

8. The pharmaceutical product of claim 1, wherein aid polymer comprises polyethylene terephthalate.

9. The pharmaceutical product of claim 7, wherein said container has an average wall thickness of at least about 0.3 mm.

10. The pharmaceutical product of claim 7, wherein said container has an average wall thickness of at least about 0.5 mm.

11. The pharmaceutical product of claim 7, wherein said container has an average wall thickness of at least about 0.9 mm.

12. The pharmaceutical product of claim 9, wherein said container has an surface area of at least about 30 cm².

13. The pharmaceutical product of claim 10, wherein said container has an surface area of at least about 30 cm².

14. The pharmaceutical product of claim 11, wherein said container has an surface area of at least about 30 cm².

15. The pharmaceutical product of claim 1, wherein said means for sealing said opening comprises a stopper.

16. The pharmaceutical product of claim 15, wherein said means for sealing said opening further comprises a seal which entirely surrounds and covers said stopper.

17. The pharmaceutical product of claim 15, wherein said stopper is pierceable by a hypodermic needle.

18. The pharmaceutical product of claim 16, wherein said seal which entirely surrounds and covers said stopper is a flip-off seal.

19. A pharmaceutical product comprising an aqueous solution of acyclovir sodium in a sealed container, wherein said solution has a shelf life in said sealed container of at least about 18 months.

20. The pharmaceutical product of claim 19 wherein said shelf life in said container is at least about 24 months.

21. The pharmaceutical product of claim 19, wherein said container is constructed of a polymer.

22. The pharmaceutical product of claim 21, wherein said polymer is polypropylene.

23. The pharmaceutical product of claim 21, wherein said polymer is polyethylene terephthalate.

24. The pharmaceutical product of claim 21, wherein said polymer has a $CO_2$ permeation constant of not more than about $1 \times 10^{-8}$ cc/cm²/mm/sec/cmHg.

25. A method of storing an aqueous solution of acyclovir sodium comprising the steps of:
   (a) providing a predetermined volume of an aqueous solution of acyclovir sodium;
   (b) providing a container constructed of a polymer having a $CO_2$ permeation constant of not more than about $1 \times 10^{-8}$ cc/cm²/mm/sec/cmHg, said container defining an opening;
   (c) placing said aqueous solution of acyclovir sodium in said container; and
   (d) sealing said opening to provide a sealed container having a $CO_2$ permeation constant of not more than about $1 \times 10^{-8}$ cc/cm²/mm/sec/cmHg.

26. The method of claim 25, wherein said aqueous solution of acyclovir sodium comprises not less than about 5 mg/mL of acyclovir sodium.

27. The method of claim 25, wherein said aqueous solution of acyclovir sodium comprises not less than about 50 mg/mL of acyclovir sodium.

28. The method of claim 25, wherein the initial pH of said aqueous solution of acyclovir, at the time of preparation under an inert atmosphere, is not less than about 11.0.

29. The method of claim 25, wherein said polymer comprises polypropylene.

30. The method of claim 25, wherein said polymer comprises polyethylene terephthalate.

31. A method of maintaining the pH of an aqueous solution of acyclovir sodium comprising storing said aqueous solution of acyclovir sodium according to the method of claim 25.

32. A method of preventing the precipitation of acyclovir from an aqueous solution of acyclovir sodium comprising storing said aqueous solution of acyclovir sodium according to the method of claim 25.

33. A pharmaceutical product comprising an aqueous solution of acyclovir sodium within a sealed container, wherein said sealed container has a $CO_2$ permeation rate of not more than about $2.6 \times 10^{-3}$ cc of $CO_2$ per mL acyclovir solution per month under normal atmospheric conditions.

34. The pharmaceutical product of claim 33, wherein said sealed container has a $CO_2$ permeation rate of not more than about $2.0 \times 10^{-3}$ cc of $CO_2$ per mL acyclovir solution per month under normal atmospheric conditions.

35. The pharmaceutical product of claim 33, wherein said sealed container has a $CO_2$ permeation rate of not more than about $1.5 \times 10^{-3}$ cc of $CO_2$ per mL acyclovir solution per month under normal atmospheric conditions.

36. The pharmaceutical product of claim 33, wherein said container is constructed of polypropylene.

* * * * *

UNITED STATES PATENT AND TRADEMARK OFFICE
CERTIFICATE OF CORRECTION

PATENT NO.    : 6,136,814
DATED         : October 24, 2000
INVENTOR(S)   : Jane Huey-Jiuan Li et al.

It is certified that error appears in the above-identified patent and that said Letters Patent is hereby corrected as shown below:

<u>Title page,</u>
Item [73], Assignee, should read as follows:

-- [73] Assignee: American Pharmaceutical Partners, Inc.,
                  Santa Monica, Calif. --.

Signed and Sealed this

Twenty-third Day of July, 2002

*Attest:*

JAMES E. ROGAN
*Attesting Officer*  *Director of the United States Patent and Trademark Office*